(12) United States Patent
Reddy et al.

(10) Patent No.: US 8,987,267 B2
(45) Date of Patent: Mar. 24, 2015

(54) 2-SUBSTITUTED-8-ALKYL-7-OXO-7,8-DIHYDROPYRIDO[2,3-D]PYRIMIDINE-6-CARBONITRILES AND USES THEREOF IN TREATING PROLIFERATIVE DISORDERS

(75) Inventors: E. Premkumar Reddy, Villanova, PA (US); M. V. Ramana Reddy, Upper Darby, PA (US)

(73) Assignee: Temple University—of the Commonwealth System of Higher Education, Philadelphia, PA (US)

( * ) Notice: Subject to any disclaimer, the term of this patent is extended or adjusted under 35 U.S.C. 154(b) by 46 days.

(21) Appl. No.: 13/813,023

(22) PCT Filed: Jul. 21, 2011

(86) PCT No.: PCT/US2011/044807
§ 371 (c)(1),
(2), (4) Date: Jan. 29, 2013

(87) PCT Pub. No.: WO2012/018540
PCT Pub. Date: Feb. 9, 2012

(65) Prior Publication Data
US 2013/0131058 A1 May 23, 2013

Related U.S. Application Data

(60) Provisional application No. 61/370,946, filed on Aug. 5, 2010.

(51) Int. Cl.
| | |
|---|---|
| *A61K 31/496* | (2006.01) |
| *A61K 31/519* | (2006.01) |
| *A61K 31/5377* | (2006.01) |
| *C07D 403/02* | (2006.01) |
| *C07D 413/02* | (2006.01) |
| *C07D 487/04* | (2006.01) |
| *C07D 471/04* | (2006.01) |

(52) U.S. Cl.
CPC .................................. *C07D 471/04* (2013.01)
USPC .................... 514/248; 514/234.5; 514/252.16; 544/117; 544/279; 544/359

(58) Field of Classification Search
CPC .............. A61K 31/496; A61K 31/519; A61K 31/5377; C07D 403/02; C07D 413/02; C07D 487/04
USPC .......... 514/234.5, 248, 252.16; 544/117, 279, 544/359
See application file for complete search history.

(56) References Cited

U.S. PATENT DOCUMENTS

| | | | |
|---|---|---|---|
| 5,620,981 A | 4/1997 | Blankley et al. | 514/258 |
| 5,733,914 A | 3/1998 | Blankley et al. | 514/258 |
| 6,498,163 B1 | 12/2002 | Boschelli et al. | 514/264.1 |
| 6,936,612 B2 | 8/2005 | Barvian et al. | 514/252.16 |
| 7,208,489 B2 | 4/2007 | Barvian et al. | 514/217.06 |
| 2001/0027196 A1 | 10/2001 | Borroni et al. | 514/256 |
| 2004/0224958 A1 | 11/2004 | Booth et al. | 514/252.16 |
| 2005/0182078 A1 | 8/2005 | Barvian et al. | 514/264.11 |
| 2006/0142312 A1 | 6/2006 | Flamme et al. | 514/264.1 |
| 2007/0179118 A1 | 8/2007 | Barvian et al. | 514/81 |
| 2008/0004285 A1 | 1/2008 | De Jonghe et al. | 514/252.16 |
| 2009/0062274 A1 | 3/2009 | Baik et al. | 514/234.2 |
| 2012/0269831 A1 | 10/2012 | Reddy et al. | 424/178.1 |

FOREIGN PATENT DOCUMENTS

| | | | | |
|---|---|---|---|---|
| WO | WO 01/70741 | 9/2001 | | C07D 471/04 |
| WO | WO 2005/105097 | 11/2005 | | A61K 31/513 |
| WO | WO 2008/016682 | 2/2008 | | A61K 31/553 |
| WO | WO 2008/047307 | 4/2008 | | C07D 471/04 |
| WO | WO 2008/150260 | 12/2008 | | C07D 471/04 |
| WO | WO 2012/018540 | * | 2/2012 | |

OTHER PUBLICATIONS

Jordan, V. C. Nature Reviews: Drug Discovery, 2, 2003, 205.*
Hackam, et al. JAMA, 296(14), 2006, 1731-1732.*
Barvian, et al., "Pyrido[2,3-*d*]pyrimidin-7-one Inhibitors of Cyclin-Dependent Kinases", *J. Med. Chem.* 2000, 43, 4606-1616.
Boschelli, et al., "Synthesis and Tyrosine Kinase Inhibitory Activity of a Series of 2-Amino-8*H*-pyrido[2,3-*d*]pyrimidines: Identification of Potent, Selective Platelet-Derived Growth Factor Receptor Tyrosine Kinase Inhibitors", *J. Med. Chem.* 1998, 41, 4365-4377.
Ikuta, et al., "Crystallographic Approach to Identification of Cyclin-dependent Kinase 4 (CDK4)-specific Inhibitors by Using CDK4 Mimic CDK2 Protein", *The Journal of Biological Chemistry*, vol. 276, No. 29, pp. 27548-27554, 2001.
Klutchko, et al., "2-Substituted Aminopyrido[2,3-*d*]pyrimidin-7(8 *H*)-ones. Structure-Activity Relationships Against Selected Tyrosine Kinases and in Vitro and in Vivo Anticancer Activity", J. Med. Chem. 1998, 41, 3276-3292.
Toogood, et al., "Discovery of a Potent and Selective Inhibitor of Cyclin-Dependent Kinase 4/6", *J. Med. Chem.* 2005, 48, 2388-2406.
Trumpp-Kallmeyer, et al., "Development of a Binding Model to Protein Tyrosine Kinases for Substituted Pyrido[2,3-*d*]pyrimidine Inhibitors", *J. Med. Chem.* 1998, 41, 1752-1763.
VanderWel, et al., "Pyrido[2,3-d]pyrimidin-7-ones as Specific Inhibitors of Cyclin-Dependent Kinase 4", *J. Med. Chem.* 2005, 48, 2371-2387.
Katritzky et al., "Synthesis and Reactivity of 2, 6-Diamino-4-methyl-3-pyridinecarbonitrile", Journal of Heterocyclic Chemistry 32(3):1-18 (1995).

* cited by examiner

*Primary Examiner* — Douglas M Willis
(74) *Attorney, Agent, or Firm* — Drinker Biddle & Reath LLP

(57) ABSTRACT

Compounds according to Formula (I), as well salts thereof: wherein $R^1$ and $R^2$ are as defined herein, are useful as antiproliferative agents and kinase inhibitors. Synthetic methods for preparing the compounds of Formula (I) are also provided.

(I)

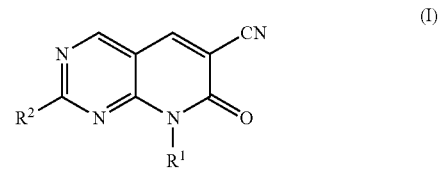

27 Claims, 1 Drawing Sheet

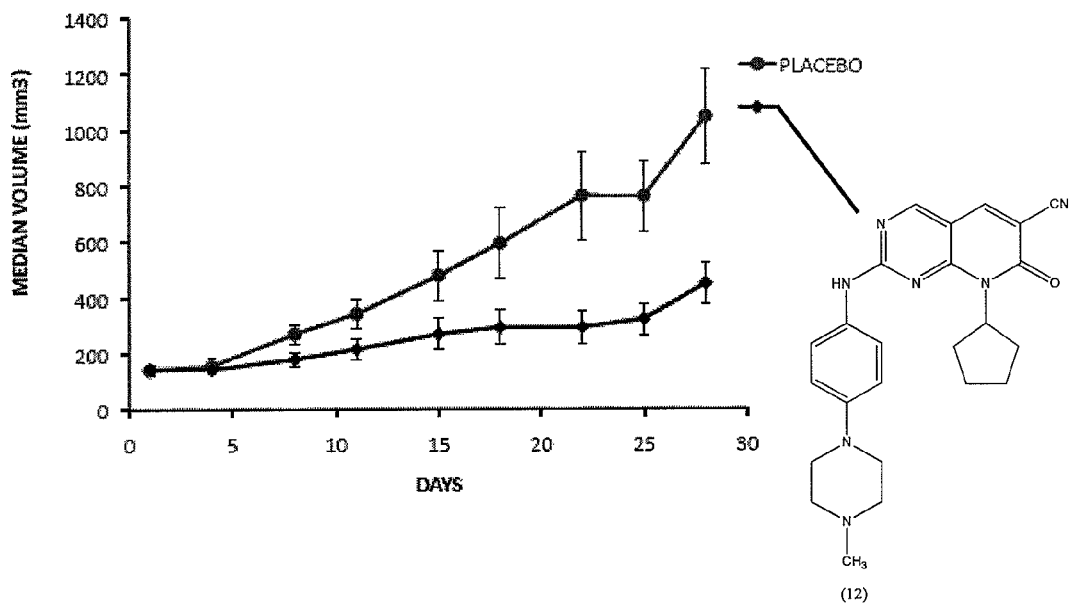

2-SUBSTITUTED-8-ALKYL-7-OXO-7,8-DIHYDROPYRIDO[2,3-D]PYRIMIDINE-6-CARBONITRILES AND USES THEREOF IN TREATING PROLIFERATIVE DISORDERS

CROSS-REFERENCE TO RELATED APPLICATION

The benefit of the filing date of U.S. Provisional Patent Application No. 61/370,946, filed Aug. 5, 2010, is hereby claimed. The entire disclosure of the aforesaid application is incorporated herein by reference.

FIELD OF THE INVENTION

The invention relates to compounds, methods for their preparation, compositions including them and methods for the treatment of cellular proliferative disorders, including, but not limited to, cancer.

BACKGROUND OF THE INVENTION

Cellular proliferative orders such as cancer are among the most common causes of death in developed countries. For diseases for which treatments exist, such as cancer, despite continuing advances, the existing treatments have undesirable side effects and limited efficacy. Identifying new effective drugs for cellular proliferative disorders, including cancer, is a continuing focus of medical research.

SUMMARY OF THE INVENTION

It has been found that certain compounds and compositions are useful for the treatment of cancer and other cellular proliferative disorders. The biologically active compounds of the invention are 2-substitued-8-alkyl-7-oxo-7,8-dihydropyrido[2,3-d]pyrimidine-6-carbonitriles.

In certain embodiments, compounds according to Formula I, or a salt thereof,

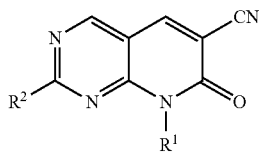

Formula I are provided.
In a compound of Formula I,
$R^1$ is $(C_1-C_6)$alkyl or $(C_3-C_8)$cycloalkyl;
$R^2$ is 4-(4-methylpiperazin-1-yl)anilinyl, 4-morpholinoanilinyl, or

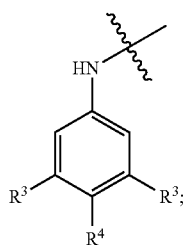

$R^3$ is independently at each occurrence $(C_1-C_6)$alkoxy; and
$R^4$ is H or $(C_1-C_6)$alkoxy.

In particular embodiments, $R^2$ is 4-(4-methylpiperazin-1-yl)anilinyl.
In some embodiments, $R^1$ is $(C_3-C_8)$cycloalkyl.
In particular embodiments, $R^1$ is cyclopentyl or cyclohexyl.
In some embodiments, $R^2$ is

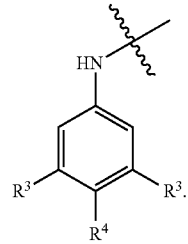

In particular embodiments, $R^1$ is cyclopentyl.
In certain embodiments, each occurrence of $R^3$ is methoxy.
In some embodiments, $R^4$ is hydrogen.
In some embodiments, $R^4$ is methoxy.
In some embodiments, $R^2$ is 4-morpholinoanilinyl.
In certain embodiments, $R^1$ is cyclopentyl.
In certain embodiments, the compound of Formula I is selected from the group consisting of 8-cyclopentyl-2-((4-(4-methylpiperazin-1-yl)phenyl)amino)-7-oxo-7,8-dihydropyrido[2,3-d]pyrimidine-6-carbonitrile; 8-cyclohexyl-2-((4-(4-methylpiperazin-1-yl)phenyl)amino)-7-oxo-7,8-dihydropyrido[2,3-d]pyrimidine-6-carbonitrile; 8-cyclopentyl-2-((3,5-dimethoxyphenyl)amino)-7-oxo-7,8-dihydropyrido[2,3-d]pyrimidine-6-carbonitrile; 8-cyclopentyl-7-oxo-2-((3,4,5-trimethoxyphenyl)amino)-7,8-dihydropyrido[2,3-d]pyrimidine-6-carbonitrile; and 8-cyclopentyl-2-((4-morpholinophenyl)amino)-7-oxo-7,8-dihydropyrido[2,3-d]pyrimidine-6-carbonitrile.

In particular embodiments, the compound according to Formula I is 8-cyclopentyl-2-((4-(4-methylpiperazin-1-yl)phenyl)amino)-7-oxo-7,8-dihydropyrido[2,3-d]pyrimidine-6-carbonitrile or a salt thereof.

The present invention further provides a pharmaceutical composition comprising a pharmaceutically acceptable carrier and a compound according to Formula I, or a pharmaceutically acceptable salt thereof.

In some embodiments, the pharmaceutical composition includes a compound of Formula I selected from the group consisting of 8-cyclopentyl-2-((4-(4-methylpiperazin-1-yl)phenyl)amino)-7-oxo-7,8-dihydropyrido[2,3-d]pyrimidine-6-carbonitrile; 8-cyclohexyl-2-((4-(4-methylpiperazin-1-yl)phenyl)amino)-7-oxo-7,8-dihydropyrido[2,3-d]pyrimidine-6-carbonitrile; 8-cyclopentyl-2-((4-(3,5-dimethoxyphenyl)amino)-7-oxo-7,8-dihydropyrido[2,3-d]pyrimidine-6-carbonitrile; 8-cyclopentyl-7-oxo-2-((4-(3,4,5-trimethoxyphenyl)amino)-7,8-dihydropyrido[2,3-d]pyrimidine-6-carbonitrile; 8-cyclopentyl-2-((4-morpholinophenyl)amino)-7-oxo-7,8-dihydropyrido[2,3-d]pyrimidine-6-carbonitrile; and pharmaceutically acceptable salts thereof.

The present invention also provides a method of treating an individual for a cellular proliferative disorder, comprising administering to the individual an effective amount of at least one compound according to Formula I, or a salt thereof.

In certain embodiments, the cellular proliferative disorder is selected from the group consisting of hemangiomatosis in newborn, secondary progressive multiple sclerosis, atherosclerosis, chronic progressive myelodegenerative disease, neurofibromatosis, ganglioneuromatosis, keloid formation, Paget's disease of the bone, fibrocystic disease of the breast, uterine fibroids, Peyronie's disease, Dupuytren's disease, restenosis, benign proliferative breast disease, benign prostatic hyperplasia, X linked lymphocellular proliferative disorder, post transplantation lymphocellular proliferative disorder, macular degeneration, retinopathies, proliferative vitreoretinopathy and non cancerous lymphocellular proliferative disorders.

In particular embodiments, the cellular proliferative disorder is cancer. In some embodiments, the cancer is selected from the group consisting of ovarian cancer; cervical cancer; breast cancer; prostate cancer; testicular cancer, lung cancer, renal cancer; colorectal cancer; skin cancer; brain cancer; leukemia, including acute myeloid leukemia, chronic myeloid leukemia, acute lymphoid leukemia, and chronic lymphoid leukemia.

The present invention further provides a method of inducing apoptosis of cancer cells in an individual afflicted with cancer, comprising administering to the individual an effective amount of at least one compound according to Formula I, or a salt thereof.

In some embodiments, the cancer cells are tumor cells. In particular embodiments, the tumor cells are selected from the group consisting of ovarian, cervical, uterine, vaginal, breast, prostate, testicular, lung, renal, colorectal, stomach, adrenal, mouth, esophageal, hepatic, gall bladder, bone, lymphatic, eye, skin, and brain tumor cells.

The present invention further provides a process for the preparation of a compound according to Formula I. In some embodiments, the process comprises treating a compound of Formula II

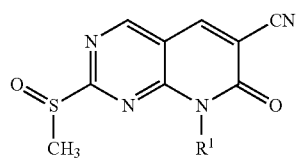

Formula II with an amine selected from the group consisting of 4-(4-methylpiperazin-1-yl)aniline, 4-morpholinoaniline, and

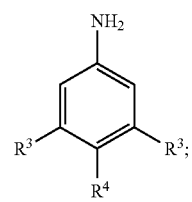

wherein $R^1$ is $(C_1-C_6)$alkyl or $(C_3-C_8)$cycloalkyl; $R^3$ is independently at each occurrence $(C_1-C_6)$alkoxy; and $R^4$ is H or $(C_1-C_6)$alkoxy. The process further includes obtaining a compound according to Formula I.

In some embodiments, a compound of Formula II is prepared by reacting a compound of Formula III

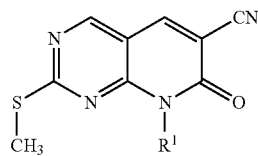

Formula III with an oxidant.

In some embodiments, a compound of Formula III is prepared by reacting a compound of Formula IV

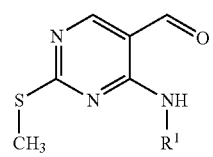

Formula IV with 2-cyanoacetic acid in the presence of benzylamine and acetic acid.

In some embodiments, a compound of Formula IV is prepared by selectively oxidizing a compound of Formula V

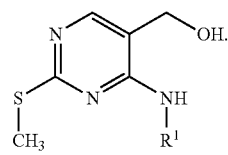

Formula V

In some embodiments, a compound of Formula V is prepared by reducing a compound of Formula VI

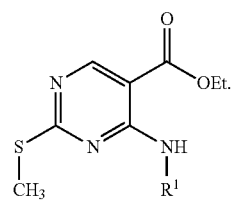

Formula VI

In further embodiments, a compound of Formula VI is prepared by reacting a compound of Formula VII

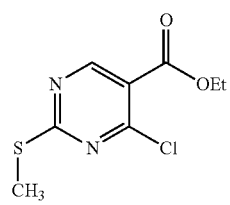

Formula VII with an amine having the formula $NH_2R^1$.

The present invention further provides a method of inhibiting kinase activity in a mammal in need of such treatment, said method comprising administering a therapeutically effective amount of a compound of Formula I, or a pharmaceutically acceptable salt thereof.

DETAILED DESCRIPTION OF THE INVENTION

The compounds and compositions of the invention are believed to selectively inhibit proliferation of cancer cells, and kill various tumor cell types. The compounds of the invention inhibit various protein kinases. Although similar compounds have been reported to inhibit kinase activity (see, for example U.S. Pat. No. 6,498,163), the compounds of the present invention have a surprisingly different kinase inhibition profile and inhibit a wider range of protein kinases.

The compounds of the invention are believed to inhibit the proliferation of tumor cells, and for some compounds, induce cell death. Cell death results from the induction of apoptosis. The compounds are believed effective against a broad range of tumor types, including but not limited to the following: ovarian cancer, breast cancer, prostate cancer, lung cancer, renal cancer, colorectal cancer, brain cancer and leukemia.

The compounds are also believed useful in the treatment of non-cancer cellular proliferative disorders, including but not limited to the following: hemangiomatosis in newborn, secondary progressive multiple sclerosis, chronic progressive myelodegenerative disease, neurofibromatosis, ganglioneuromatosis, keloid formation, Paget's disease of the bone, fibrocystic disease of the breast, uterine fibroids, Peyronie's disease, Dupuytren's disease, restenosis and cirrhosis.

BRIEF DESCRIPTION OF THE DRAWINGS

The foregoing summary, as well as the following detailed description the embodiments, will be better understood when read in conjunction with the appended drawings. For the purpose of illustration, there are shown in the drawings some embodiments which may be preferable. It should be understood, however, that the embodiments depicted are not limited to the precise arrangements and instrumentalities shown.

FIG. 1 is a graph showing the efficacy of 8-cyclopentyl-2-((4-(4-methylpiperazin-1-yl)phenyl)amino)-7-oxo-7,8-dihydropyrido[2,3-d]pyrimidine-6-carbonitrile at inhibiting growth of Colo-205 tumor fragments implanted in female athymic nude mice.

I. DEFINITIONS

A. General

As used in the specification and the appended claims, the singular forms "a," "an" and "the" include plural referents unless the context clearly dictates otherwise.

As used herein, the terms "treat" and "treatment" are used interchangeably and are meant to indicate a postponement of development of a disorder and/or a reduction in the severity of symptoms that will or are expected to develop. The terms further include ameliorating existing symptoms, preventing additional symptoms, and ameliorating or preventing the underlying metabolic causes of symptoms.

As used herein, "individual" (as in the subject of the treatment) means both mammals and non-mammals. Mammals include, for example, humans; non-human primates, e.g. apes and monkeys; cattle; horses; sheep; and goats. Non-mammals include, for example, fish and birds.

The expression "effective amount", when used to describe therapy to an individual suffering from a cancer or other cellular proliferative disorder, refers to the amount of a compound according to Formula I that inhibits the abnormal growth or proliferation, or alternatively induces apoptosis of cancer cells, preferably tumor cells, resulting in a therapeutically useful and selective cytotoxic effect on proliferative cells.

The term "cellular proliferative disorder" means a disorder wherein unwanted cell proliferation of one or more subsets of cells in a multicellular organism occurs. In some such disorders, cells are made by the organism at an atypically accelerated rate.

B. Chemical

In the following paragraphs some of the definitions include examples. The examples are intended to be illustrative, and not limiting.

The term "alkyl", by itself or as part of another substituent means, unless otherwise stated, a straight, branched or cyclic chain hydrocarbon (cycloalkyl) having the number of carbon atoms designated (i.e. $C_1$-$C_6$ means one to six carbons) and includes straight, branched chain or cyclic groups. Examples include: methyl, ethyl, propyl, isopropyl, butyl, isobutyl, tert-butyl, pentyl, neopentyl, hexyl, cyclohexyl and cyclopropylmethyl. Preferred alkyl groups are ($C_1$-$C_3$)alkyl, particularly methyl, ethyl and isopropyl. Preferred cycloalkyl groups include ($C_3$-$C_8$)cycloalkyl, with the most preferred ($C_3$-$C_8$) cycloalkyl groups being cyclopentyl and cyclohexyl.

The term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy (isopropoxy) and the higher homologs and isomers. Preferred are ($C_1$-$C_3$)alkoxy, particularly ethoxy and methoxy.

The term "cyano" refers to a —C≡N group.

The terms "halo" or "halogen" by themselves or as part of another substituent mean, unless otherwise stated, a monovalent fluorine, chlorine, bromine, or iodine atom, preferably, fluorine, chlorine, or bromine, more preferably, fluorine or chlorine.

The term "aromatic" generally refers to a carbocycle or heterocycle having one or more polyunsaturated rings having aromatic character (i.e. having (4n+2) delocalized π (pi) electrons where n is an integer).

II. Compounds of the Invention

Compounds of the invention include the compounds of Formula I, as well as salts thereof:

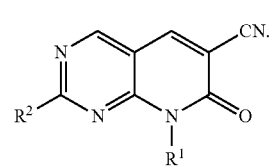

Formula I

In Formula I, $R^1$ is ($C_1$-$C_6$)alkyl or ($C_3$-$C_8$)cycloalkyl. In preferred embodiments, $R^1$ can be cyclopentyl or cyclohexyl, most preferably cyclopentyl.

$R^2$ is 4-(4-methylpiperazin-1-yl)anilinyl, 4-morpholinoanilinyl, or

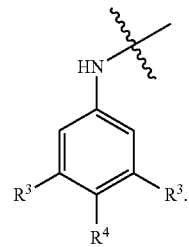

$R^3$ is independently at each occurrence ($C_1$-$C_6$)alkoxy, preferably methoxy or ethoxy, most preferably methoxy.

$R^4$ is H or ($C_1$-$C_6$)alkoxy. When $R^4$ is ($C_1$-$C_6$)alkoxy, preferably it is either ethoxy or methoxy, most preferably methoxy.

In some embodiments, each occurrence of $R^3$ is methoxy and $R^4$ is hydrogen. In other embodiments, each occurrence of $R^3$ as well as $R^4$ are methoxy.

The following compounds of the invention were prepared: 8-cyclopentyl-2-((4-(4-(4-methylpiperazin-1-yl)phenyl)amino)-7-oxo-7,8-dihydropyrido[2,3-d]pyrimidine-6-carbonitrile, 8-cyclopentyl-2-((4-morpholinophenyl)amino)-7-oxo-7,8-dihydropyrido[2,3-d]pyrimidine-6-carbonitrile, 8-cyclopentyl-2-((3,5-dimethoxyphenyl)amino)-7-oxo-7,8-dihydropyrido[2,3-d]pyrimidine-6-carbonitrile, 8-cyclopentyl-2-((3,5-dimethoxyphenyl)amino)-7-oxo-7,8-dihydropyrido[2,3-d]pyrimidine-6-carbonitrile, and 8-cyclohexyl-2-((4-(4-methylpiperazin-1-yl)phenyl)amino)-7-oxo-7,8-dihydropyrido[2,3-d]pyrimidine-6-carbonitrile.

Other exemplary compounds within the scope of the present invention include the following, and salts thereof: 8-cyclohexyl-2-((4-morpholinophenyl)amino)-7-oxo-7,8-dihydropyrido[2,3-d]pyrimidine-6-carbonitrile, 8-cyclohexyl-2-((3,5-dimethoxyphenyl)amino)-7-oxo-7,8-dihydropyrido[2,3-d]pyrimidine-6-carbonitrile, 8-cyclohexyl-7-oxo-2-((3,4,5-trimethoxyphenyl)amino)-7,8-dihydropyrido[2,3-d]pyrimidine-6-carbonitrile, 8-cyclopropyl-7-oxo-2-((3,4,5-trimethoxyphenyl)amino)-7,8-dihydropyrido [2,3-d]pyrimidine-6-carbonitrile, 8-cyclobutyl-7-oxo-2-((3,4,5-trimethoxyphenyl)amino)-7,8-dihydropyrido[2,3-d]pyrimidine-6-carbonitrile, 8-cyclobutyl-2-((3,5-dimethoxyphenyl)amino)-7-oxo-7,8-dihydropyrido[2,3-d]pyrimidine-6-carbonitrile, 8-cyclopropyl-2-((3,5-dimethoxyphenyl)amino)-7-oxo-7,8-dihydropyrido[2,3-d]pyrimidine-6-carbonitrile, 8-cyclopropyl-2-((4-(4-methylpiperazin-1-yl)phenyl)amino)-7-oxo-7,8-dihydropyrido[2,3-d]pyrimidine-6-carbonitrile, 8-cyclobutyl-2-((4-(4-methylpiperazin-1-yl)phenyl)amino)-7-oxo-7,8-dihydropyrido[2,3-d]pyrimidine-6-carbonitrile, 8-cyclobutyl-2-((4-morpholinophenyl)amino)-7-oxo-7,8-dihydropyrido[2,3-d]pyrimidine-6-carbonitrile, and 8-cyclopropyl-2-((4-morpholinophenyl)amino)-7-oxo-7,8-dihydropyrido[2,3-d]pyrimidine-6-carbonitrile.

It is to be understood that other particular and preferred embodiments of the compounds of the invention will combine the features of the particular and preferred embodiments of the invention explicitly described above. Embodiments defined by such combinations are contemplated as particular embodiments of the invention.

In other preferred embodiments, the compound of Formula I, or any of the embodiments thereof, is an isolated compound. In other preferred embodiments, the compound of Formula I, and compositions containing the compounds, including pharmaceutical compositions, are substantially free of pharmaceutically unacceptable contaminants. A pharmaceutically unacceptable contaminant is a substance which, if present in more than an insubstantial amount, would render the compound or composition unsuitable for use as a pharmaceutical for therapeutic administration. Examples include toxic materials such as halogenated solvents and heavy metals, and potentially infectious materials such as bacteria, fungi, viruses, and bacterial and fungal spores.

III. Methods for Preparing Compounds of the Invention and Intermediates Useful in the Synthesis of Compounds of the Invention The present invention provides processes for preparing compounds according to Formula I, intermediates that are useful in the preparation of such compounds, and processes for preparing such intermediates.

The compounds can be prepared by a variety of synthetic routes. Representative procedures are shown in Schemes 1-5. It will be readily apparent that the compounds can be synthesized by substitution of the appropriate starting materials, reactants, and reagents in the syntheses shown below, with $R^1$, $R^2$, $R^3$, and $R^4$ defined as previously set forth herein. It will also be apparent that the order of the steps themselves can be changed, depending on the nature of the reactions. Precursor compounds, intermediates, and reagents are commercially available or can be prepared from commercially available starting materials. The following schemes are representative, and are in no way intended to limit the scope of the compounds in the embodiments of the present invention.

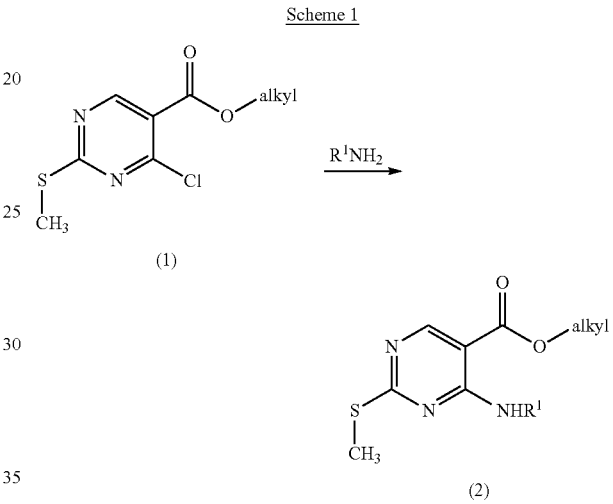

Scheme 1

A synthesis of compounds of formula (2) is shown in Scheme 1. Compounds of formula (2) can be prepared by reacting a commercially available 4-halopyrimidine carboxylate such as a compound of formula (1) with an amine, $R^1$—$NH_2$, in the presence of a base in a polar or aprotic solvent. Useful bases include organic bases, for example, tertiary amines such as diisopropylethylamine (DIPEA) or triethylamine (TEA). Useful solvents can include tetrahydrofuran (THF), acetonitrile, p-dioxane, or N,N,-dimethylformamide (DMF). The reaction can be heated, to the extent necessary, at a temperature appropriate for a given solvent.

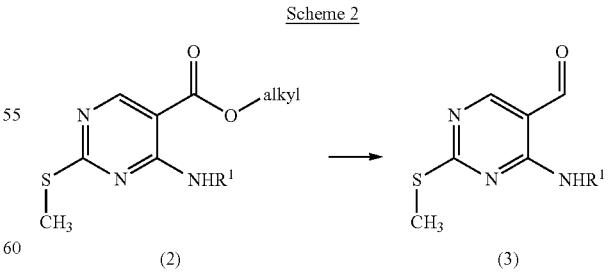

Scheme 2

A synthesis of compounds according to formula (3) is shown in Scheme 2. Ester (2) can be reduced using a reducing agent such as lithium aluminum hydride (LAH) in a polar solvent, to provide an alcohol intermediate. Other useful reducing agents include diisobutylaluminum hydride (DIBAL-H, 2 equivalents), borane-THF complex, and the like. Useful solvents include tetrahydrofuran (THF), diethyl ether, and the like. The intermediate alcohol can be oxidized to aldehyde (3) using an oxidizing agent such as manganese dioxide in a halogenated solvent. Other useful oxidizing agents capable of oxidizing an alcohol to an aldehyde, such as for example only, Dess-Martin periodinane, are well known in the art. Useful halogenated solvents include dichloromethane, chloroform, and the like.

In an alternative embodiment, the ester (2) can be converted directly to aldehyde (3) by treatment with 1 equivalent of DIBAL-H at an appropriate temperature in a solvent such as dichloromethane, THF, or toluene.

Scheme 3

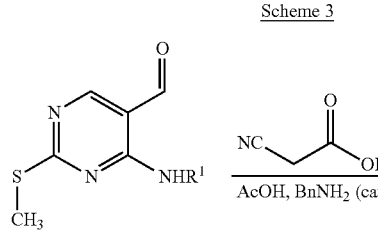

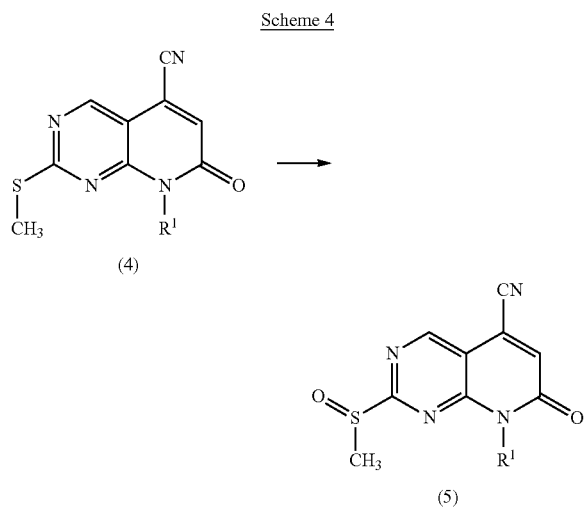

A synthesis of compounds according to formula (4) is provided in Scheme 3. According to Scheme 3, compounds of formula (3) can be condensed with cyanoacetic acid in acetic acid, to provide a compound of formula (4). A catalytic amount of benzylamine can be used in the condensation reaction. Temperatures for the condensation reaction can range from about 100° C. to about 120° C. (reflux).

A synthesis of compounds according to formula (5) is shown in Scheme 4. The compound of formula (4) can be oxidized to a sulfoxide by treating (4) with an oxidizing agent. Useful oxidizing agents can include, but are not limited to, meta-chloroperoxybenzoic acid (m-CPBA), hydrogen peroxide, sodium hypochlorite, sodium periodate, tert-butyl hypochlorite, and peracids such as peracetic acid. Stoichiometric use of the oxidizing agent can be employed if necessary to control the oxidation state of sulfur. Useful solvents include acetic acid and halogenated solvents such as chloroform or dichloromethane, and the like. A preferred oxidizing reagent is m-CPBA in dichloromethane.

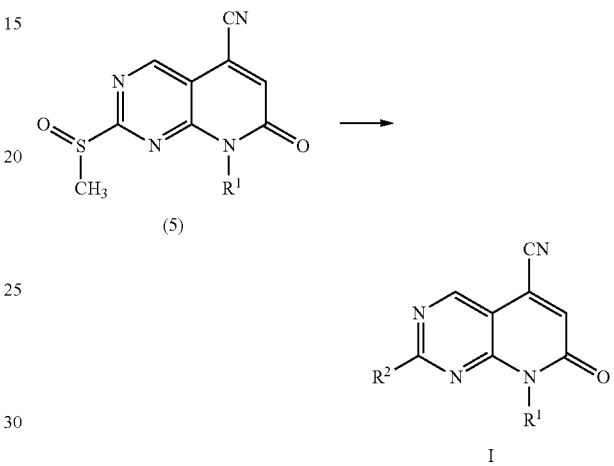

Synthesis of a compound according to Formula I is shown in Scheme 5. The compound of Formula (5) can be treated with an amine compound having the formula $R^2$—$NH_2$ to provide a compound of Formula I. $R^2$ can be as defined previously herein. Exemplary solvents suitable for this reaction include benzenoid solvents such as toluene, o-xylene, m-xylene, p-xylene, xylene mixtures, anisole, and mixtures thereof. Other useful solvents include p-dioxane, 1,2-dimethoxyethane (DME), THF, and the like. Useful temperatures to affect reaction can range from about 65° C. to about 150° C., dependent upon the solvent used. A molar excess of the amine $R^2$—$NH_2$ can be used, including anywhere from about 1.05 to about 2.0 equivalents.

The above-described reactions, unless otherwise noted, are usually conducted at a pressure of about one to about three atmospheres, preferably at ambient pressure (about one atmosphere).

The present invention further embraces isolated compounds according to Formula I. The expression "isolated compound" refers to a preparation of a compound of Formula I, or a mixture of compounds according to Formula I, wherein the isolated compound has been separated from the reagents used, and/or byproducts formed, during the synthesis of the compound or compounds. "Isolated" does not mean that the preparation is technically pure (homogeneous), but it is sufficiently pure to compound in a form in which it can be used therapeutically. Preferably an "isolated compound" refers to a preparation of a compound of Formula I or a mixture of compounds according to Formula I, which contains the named compound or mixture of compounds according to Formula I in an amount of at least 10 percent by weight of the total weight. Preferably the preparation contains the named compound or mixture of compounds in an amount of at least 50 percent by weight of the total weight; more preferably at least 80 percent by weight of the total weight; and most preferably at least 90 percent, at least 95 percent or at least 98 percent by weight of the total weight of the preparation.

The compounds of the invention and intermediates may be isolated from their reaction mixtures and purified by standard techniques such as filtration, liquid-liquid extraction, solid phase extraction, distillation, recrystallization or chromatography, including flash column chromatography, or HPLC. The preferred method for purification of the compounds according to Formula I or salts thereof comprises crystallizing the compound or salt from a solvent to form, preferably, a crystalline form of the compounds or salts thereof. Following crystallization, the crystallization solvent is removed by a process other than evaporation, for example filtration or decanting, and the crystals are then preferably washed using pure solvent (or a mixture of pure solvents). Preferred solvents for crystallization include water, alcohols, particularly alcohols containing up to four carbon atoms such as methanol, ethanol, isopropanol, and butan-1-ol, butan-2-ol, and 2-methyl-2-propanol, ethers, for example diethyl ether, diisopropyl ether, t-butyl methyl ether, 1,2-dimethoxyethane, tetrahydrofuran and 1,4-dioxane, carboxylic acids, for example formic acid and acetic acid, and hydrocarbon solvents, for example pentane, hexane, toluene, and mixtures thereof, particularly aqueous mixtures such as aqueous ethanol. Pure solvents, preferably at least analytical grade, and more preferably pharmaceutical grade are preferably used. In a preferred embodiment of the processes of the invention, the products are so isolated. In the compounds of the invention according to Formula I or salt thereof, and pharmaceutical compositions thereof, the compound according to Formula I or salt thereof is preferably in or prepared from a crystalline form, preferably prepared according to such a process.

The synthetic methods described above reflect a convergent synthesis strategy. Thus two components may be synthesized and elaborated separately prior to condensing or coupling the two components to form the target compounds. These convergent synthetic schemes allow for arrangement of the assembly steps of the backbone of the target compounds and derivatization of derivatizable functionalities to accommodate functional group sensitivity and/or to allow for functional groups or elements to be introduced either before or after the assembly of the backbone of the target compounds via the condensation or coupling reactions described.

It will be appreciated by one skilled in the art that certain aromatic substituents in the compounds of the invention, intermediates used in the processes described above, or precursors thereto, may be introduced by employing aromatic substitution reactions to introduce or replace a substituent, or by using functional group transformations to modify an existing substituent, or a combination thereof. Such reactions may be effected either prior to or immediately following the processes mentioned above, and are included as part of the process aspect of the invention. The reagents and reaction conditions for such procedures are known in the art. Specific examples of procedures which may be employed include, but are not limited to, electrophilic functionalization of an aromatic ring, for example via nitration, halogenation, or acylation; transformation of a nitro group to an amino group, for example via reduction, such as by catalytic hydrogenation; acylation, alkylation, or sulfonylation of an amino or hydroxyl group; replacement of an amino group by another functional group via conversion to an intermediate diazonium salt followed by nucleophilic or free radical substitution of the diazonium salt; or replacement of a halogen by another group, for example via nucleophilic or organometallically-catalyzed substitution reactions.

Additionally, in the aforesaid processes, certain functional groups which would be sensitive to the reaction conditions may be protected by protecting groups. A protecting group is a derivative of a chemical functional group which would otherwise be incompatible with the conditions required to perform a particular reaction which, after the reaction has been carried out, can be removed to re-generate the original functional group, which is thereby considered to have been "protected". Any chemical functionality that is a structural component of any of the reagents used to synthesize compounds of this invention may be optionally protected with a chemical protecting group if such a protecting group is useful in the synthesis of compounds of this invention. The person skilled in the art knows when protecting groups are indicated, how to select such groups, and processes that can be used for selectively introducing and selectively removing them, because methods of selecting and using protecting groups have been extensively documented in the chemical literature. Techniques for selecting, incorporating and removing chemical protecting groups may be found, for example, in *Protective Groups in Organic Synthesis* by Theodora W. Greene, Peter G. M. Wuts (John Wiley & Sons, Inc. 1999), the entire disclosure of which is incorporated herein by reference.

In addition to use of a protecting group, sensitive functional groups may be introduced as synthetic precursors to the functional group desired in the intermediate or final product. An example of this is an aromatic nitro ($-NO_2$) group. The aromatic nitro group does not undergo any of the nucleophilic reactions of an aromatic amino group. However, the nitro group can serve as the equivalent of a protected amino group because it is readily reduced to the amino group under mild conditions that are selective for the nitro group over most other functional groups.

It will be appreciated by one skilled in the art that the processes described are not the exclusive means by which compounds of the invention may be synthesized and that an extremely broad repertoire of synthetic organic reactions is available to be potentially employed in synthesizing compounds of the invention. The person skilled in the art knows how to select and implement appropriate synthetic routes. Suitable synthetic methods may be identified by reference to the literature, including reference sources such as *Comprehensive Organic Synthesis*, Ed. B. M. Trost and I. Fleming (Pergamon Press, 1991), *Comprehensive Organic Functional Group Transformations*, Ed. A. R. Katritzky, O. Meth-Cohn, and C. W. Rees (Pergamon Press, 1996), *Comprehensive Organic Functional Group Transformations II*, Ed. A. R. Katritzky and R. J. K. Taylor (Editor) (Elsevier, $2^{nd}$ Edition, 2004), *Comprehensive Heterocyclic Chemistry*, Ed. A. R. Katritzky and C. W. Rees (Pergamon Press, 1984), *Comprehensive Heterocyclic Chemistry II*, Ed. A. R. Katritzky, C. W. Rees, and E. F. V. Scriven (Pergamon Press, 1996), and *Advanced Organic Chemistry*, $4^{th}$ Ed., J. March (John Wiley & Sons, 1992).

IV. Treatment of Cellular Proliferative Disorders Using Compounds of the Invention According to another embodiment of the invention, a method of treating an individual suffering from a cellular proliferative disorder, particularly cancer, is provided, comprising administering to said individual an effective amount of at least one compound according to Formula I, or a pharmaceutically acceptable salt thereof, either alone, or in combination with a pharmaceutically acceptable carrier.

According to another embodiment of the invention, a method of inducing apoptosis of cancer cells, preferably tumor cells, in an individual afflicted with cancer is provided, comprising administering to said individual an effective amount of at least one compound according to Formula I, or a pharmaceutically acceptable salt thereof, either alone, or in combination with a pharmaceutically acceptable carrier.

The invention is also directed to the use in medicine of a compound according to Formula I, or a pharmaceutically acceptable salt thereof.

The invention is also directed to compounds of Formula I, and pharmaceutically acceptable salts thereof, for treating a proliferative disorder, or for inducing apoptosis of tumor cells.

The invention is also directed to a medicament comprising a compound of Formula I, or a pharmaceutically acceptable salt thereof, for use in treating a proliferative disorder, or for inducing apoptosis of tumor cells.

The invention is also directed to the use of a compound according to Formula I, or a pharmaceutically acceptable salt thereof in the preparation of a medicament for treatment of a cellular proliferative disorder, particularly cancer, or for inducing apoptosis of tumor cells in an individual affected with cancer.

Particular and preferred embodiments of this aspect of the invention are those wherein the compound of Formula I used in the method of treatment, either alone or as part of a composition, is a particular or preferred embodiment of the compound of Formula I in the description of the compounds and compositions of the invention as provided herein.

The compounds according to the invention may be administered to individuals (mammals, including animals and humans) afflicted with a cellular proliferative disorder such as cancer, malignant and benign tumors, blood vessel proliferative disorders, autoimmune disorders, and fibrotic disorders. In a particular embodiment of the invention, the individual treated is a human.

The compounds are believed effective against a broad range of tumor types, including but not limited to the following: ovarian cancer; cervical cancer; breast cancer; prostate cancer; testicular cancer, lung cancer, renal cancer; colorectal cancer; skin cancer; brain cancer; leukemia, including acute myeloid leukemia, chronic myeloid leukemia, acute lymphoid leukemia, and chronic lymphoid leukemia.

More particularly, cancers that may be treated by the compounds, compositions and methods of the invention include, but are not limited to, the following:

cardiac cancers, including, for example sarcoma, e.g., angiosarcoma, fibrosarcoma, rhabdomyosarcoma, and liposarcoma; myxoma; rhabdomyoma; fibroma; lipoma and teratoma;

lung cancers, including, for example, bronchogenic carcinoma, e.g., squamous cell, undifferentiated small cell, undifferentiated large cell, and adenocarcinoma; alveolar and bronchiolar carcinoma; bronchial adenoma; sarcoma; lymphoma; chondromatous hamartoma; and mesothelioma;

gastrointestinal cancer, including, for example, cancers of the esophagus, e.g., squamous cell carcinoma, adenocarcinoma, leiomyosarcoma, and lymphoma; cancers of the stomach, e.g., carcinoma, lymphoma, and leiomyosarcoma; cancers of the pancreas, e.g., ductal adenocarcinoma, insulinoma, glucagonoma, gastrinoma, carcinoid tumors, and vipoma; cancers of the small bowel, e.g., adenocarcinoma, lymphoma, carcinoid tumors, Kaposi's sarcoma, leiomyoma, hemangioma, lipoma, neurofibroma, and fibroma; cancers of the large bowel, e.g., adenocarcinoma, tubular adenoma, villous adenoma, hamartoma, and leiomyoma;

genitourinary tract cancers, including, for example, cancers of the kidney, e.g., adenocarcinoma, Wilm's tumor (nephroblastoma), lymphoma, and leukemia; cancers of the bladder and urethra, e.g., squamous cell carcinoma, transitional cell carcinoma, and adenocarcinoma; cancers of the prostate, e.g., adenocarcinoma, and sarcoma; cancer of the testis, e.g., seminoma, teratoma, embryonal carcinoma, teratocarcinoma, choriocarcinoma, sarcoma, interstitial cell carcinoma, fibroma, fibroadenoma, adenomatoid tumors, and lipoma;

liver cancers, including, for example, hepatoma, e.g., hepatocellular carcinoma; cholangiocarcinoma; hepatoblastoma; angiosarcoma; hepatocellular adenoma; and hemangioma;

bone cancers, including, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochrondroma (osteocartilaginous exostoses), benign chondroma, chondroblastoma, chondromyxofibroma, osteoid osteoma and giant cell tumors;

nervous system cancers, including, for example, cancers of the skull, e.g., osteoma, hemangioma, granuloma, xanthoma, and osteitis deformans; cancers of the meninges, e.g., meningioma, meningiosarcoma, and gliomatosis; cancers of the brain, e.g., astrocytoma, medulloblastoma, glioma, ependymoma, germinoma (pinealoma), glioblastoma multiform, oligodendroglioma, schwannoma, retinoblastoma, and congenital tumors; and cancers of the spinal cord, e.g., neurofibroma, meningioma, glioma, and sarcoma;

gynecological cancers, including, for example, cancers of the uterus, e.g., endometrial carcinoma; cancers of the cervix, e.g., cervical carcinoma, and pre-tumor cervical dysplasia; cancers of the ovaries, e.g., ovarian carcinoma, including serous cystadenocarcinoma, mucinous cystadenocarcinoma, unclassified carcinoma, cone-thecal cell tumors, Sertoli-Leydig cell tumors, dysgerminoma, and malignant teratoma; cancers of the vulva, e.g., squamous cell carcinoma, intraepithelial carcinoma, adenocarcinoma, fibrosarcoma, and melanoma; cancers of the vagina, e.g., clear cell carcinoma, squamous cell carcinoma, botryoid sarcoma, and embryonal rhabdomyosarcoma; and cancers of the fallopian tubes, e.g., carcinoma;

hematologic cancers, including, for example, cancers of the blood, e.g., acute myeloid leukemia, chronic myeloid leukemia, acute lymphoblastic leukemia, chronic lymphocytic leukemia, myeloproliferative diseases, multiple myeloma, and myelodysplastic syndrome, Hodgkin's lymphoma, non-Hodgkin's lymphoma (malignant lymphoma) and Waldenström's macroglobulinemia;

skin cancers, including, for example, malignant melanoma, basal cell carcinoma, squamous cell carcinoma, Kaposi's sarcoma, moles dysplastic nevi, lipoma, angioma, dermatofibroma, keloids, psoriasis; and adrenal gland cancers, including, for example, neuroblastoma.

Cancers may be solid tumors that may or may not be metastatic. Cancers may also occur, as in leukemia, as a diffuse tissue. Thus, the term "tumor cell", as provided herein, includes a cell afflicted by any one of the above identified disorders.

The compounds are also believed useful in the treatment of non-cancer cellular proliferative disorders, that is, cellular proliferative disorders which are characterized by benign indications. Such disorders may also be known as "cytoproliferative" or "hyperproliferative" in that cells are made by the body at an atypically elevated rate. Non-cancer cellular proliferative disorders believed treatable by compounds according to the invention include, for example: hemangiomatosis in newborn, secondary progressive multiple sclerosis, atherosclerosis, chronic progressive myelodegenerative disease, neurofibromatosis, ganglioneuromatosis, keloid formation, Paget's disease of the bone, fibrocystic disease of the breast, uterine fibroids, Peyronie's disease, Dupuytren's disease, restenosis, benign proliferative breast disease, benign prostatic hyperplasia, X-linked lymphocellular proliferative disorder (Duncan disease), post-transplantation lymphocellular proliferative disorder (PTLD), macular degeneration, and retinopathies, such as diabetic retinopathies and proliferative vitreoretinopathy (PVR)

Other non-cancer cellular proliferative disorders believed treatable by compounds according to the invention include the presence of pre-cancerous lymphoproliferative cells associated with an elevated risk of progression to a cancerous disorder. Many non-cancerous lymphocellular proliferative disorders are associated with latent viral infections such as Epstein-Barr virus (EBV) and Hepatitis C. These disorders often begin as a benign pathology and progress into lymphoid neoplasia as a function of time.

V. Salts of Compounds According to the Invention

The compounds of the present invention may take the form of salts. The term "salts" embraces addition salts of free acids or free bases which are compounds of the invention. The term "pharmaceutically-acceptable salt" refers to salts which possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification or formulation of compounds of the invention.

Suitable pharmaceutically-acceptable acid addition salts may be prepared from an inorganic acid or from an organic acid. Examples of inorganic acids include hydrochloric, hydrobromic, hydriodic, nitric, carbonic, sulfuric, and phosphoric acids. Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoroacetic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid. Examples of pharmaceutically unacceptable acid addition salts include, for example, perchlorates and tetrafluoroborates.

All of these salts may be prepared by conventional means from the corresponding compound according to Formula I and the appropriate acid. Preferably the salts are in crystalline form, and preferably prepared by crystallization of the salt from a suitable solvent. The person skilled in the art will know how to prepare and select suitable salt forms for example, as described in *Handbook of Pharmaceutical Salts: Properties, Selection, and Use* By P. H. Stahl and C. G. Wermuth (Wiley-VCH 2002).

VI. Pharmaceutical Compositions

The compounds of the invention may be administered in the form of a pharmaceutical composition, in combination with a pharmaceutically acceptable carrier. The active ingredient in such formulations may comprise from 0.1 to 99.99 weight percent. "Pharmaceutically acceptable carrier" means any carrier, diluent or excipient which is compatible with the other ingredients of the formulation and not deleterious to the recipient.

The active agent is preferably administered with a pharmaceutically acceptable carrier selected on the basis of the selected route of administration and standard pharmaceutical practice. The active agent may be formulated into dosage forms according to standard practices in the field of pharmaceutical preparations. See Alphonso Gennaro, ed., *Remington's Pharmaceutical Sciences*, 18$^{th}$ Edition (1990), Mack Publishing Co., Easton, Pa. Suitable dosage forms may comprise, for example, tablets, capsules, solutions, parenteral solutions, troches, suppositories, or suspensions.

For parenteral administration, the active agent may be mixed with a suitable carrier or diluent such as water, an oil (particularly a vegetable oil), ethanol, saline solution, aqueous dextrose (glucose) and related sugar solutions, glycerol, or a glycol such as propylene glycol or polyethylene glycol. Solutions for parenteral administration preferably contain a water soluble salt of the active agent. Stabilizing agents, antioxidant agents and preservatives may also be added. Suitable antioxidant agents include sulfite, ascorbic acid, citric acid and its salts, and sodium EDTA. Suitable preservatives include benzalkonium chloride, methyl- or propyl-paraben, and chlorbutanol. The composition for parenteral administration may take the form of an aqueous or non-aqueous solution, dispersion, suspension or emulsion.

For oral administration, the active agent may be combined with one or more solid inactive ingredients for the preparation of tablets, capsules, pills, powders, granules or other suitable oral dosage forms. For example, the active agent may be combined with at least one excipient such as fillers, binders, humectants, disintegrating agents, solution retarders, absorption accelerators, wetting agents absorbents or lubricating agents. According to one tablet embodiment, the active agent may be combined with carboxymethylcellulose calcium, magnesium stearate, mannitol and starch, and then formed into tablets by conventional tableting methods.

The specific dose of a compound according to the invention to obtain therapeutic benefit for treatment of a cellular proliferative disorder will, of course, be determined by the particular circumstances of the individual patient including the size, weight, age and sex of the patient, the nature and stage of the cellular proliferative disorder, the aggressiveness of the cellular proliferative disorder, and the route of administration of the compound.

For example, a daily dosage from about 0.05 to about 50 mg/kg/day may be utilized, more preferably from about 0.1 to about 10 mg/kg/day. Higher or lower doses are also contemplated as it may be necessary to use dosages outside these ranges in some cases. The daily dosage may be divided, such as being divided equally into two to four times per day daily dosing. The compositions are preferably formulated in a unit dosage form, each dosage containing from about 1 to about 500 mg, more typically, about 10 to about 100 mg of active agent per unit dosage. The term "unit dosage form" refers to physically discrete units suitable as a unitary dosage for human subjects and other mammals, each unit containing a predetermined quantity of active material calculated to produce the desired therapeutic effect, in association with a suitable pharmaceutical excipient.

The pharmaceutical compositions of the present invention may also be formulated so as to provide slow or controlled release of the active ingredient therein using, for example, hydropropylmethyl cellulose in varying proportions to provide the desired release profile, other polymer matrices, gels, permeable membranes, osmotic systems, multilayer coatings, microparticles, liposomes and/or microspheres.

In general, a controlled-release preparation is a pharmaceutical composition capable of releasing the active ingredient at the required rate to maintain constant pharmacological activity for a desirable period of time. Such dosage forms provide a supply of a drug to the body during a predetermined period of time and thus maintain drug levels in the therapeutic range for longer periods of time than conventional non-controlled formulations.

U.S. Pat. No. 5,674,533 discloses controlled-release pharmaceutical compositions in liquid dosage forms for the administration of moguisteine, a potent peripheral antitussive. U.S. Pat. No. 5,059,595 describes the controlled-release of active agents by the use of a gastro-resistant tablet for the therapy of organic mental disturbances. U.S. Pat. No. 5,591,767 describes a liquid reservoir transdermal patch for the controlled administration of ketorolac, a non-steroidal anti-inflammatory agent with potent analgesic properties. U.S. Pat. No. 5,120,548 discloses a controlled-release drug delivery device comprised of swellable polymers. U.S. Pat. No. 5,073,543 describes controlled-release formulations containing a trophic factor entrapped by a ganglioside-liposome vehicle. U.S. Pat. No. 5,639,476 discloses a stable solid controlled-release formulation having a coating derived from an aqueous dispersion of a hydrophobic acrylic polymer. Biodegradable microparticles are known for use in controlled-release formulations. U.S. Pat. No. 5,354,566 discloses a controlled-release powder that contains the active ingredient. U.S. Pat. No. 5,733,566 describes the use of polymeric microparticles that release antiparasitic compositions.

The controlled-release of the active ingredient may be stimulated by various inducers, for example pH, temperature, enzymes, water, or other physiological conditions or compounds. Various mechanisms of drug release exist. For example, in one embodiment, the controlled-release component may swell and form porous openings large enough to release the active ingredient after administration to a patient. The term "controlled-release component" in the context of the present invention is defined herein as a compound or compounds, such as polymers, polymer matrices, gels, permeable membranes, liposomes and/or microspheres, that facilitate the controlled-release of the active ingredient in the pharmaceutical composition. In another embodiment, the controlled-release component is biodegradable, induced by exposure to the aqueous environment, pH, temperature, or enzymes in the body. In another embodiment, sol-gels may be used, wherein the active ingredient is incorporated into a sol-gel matrix that is a solid at room temperature. This matrix is implanted into a patient, preferably a mammal, having a body temperature high enough to induce gel formation of the sol-gel matrix, thereby releasing the active ingredient into the patient.

The components used to formulate the pharmaceutical compositions are of high purity and are substantially free of potentially harmful contaminants (e.g., at least National Food grade, generally at least analytical grade, and more typically at least pharmaceutical grade). Particularly for human consumption, the composition is preferably manufactured or formulated under Good Manufacturing Practice standards as defined in the applicable regulations of the U.S. Food and Drug Administration. For example, suitable formulations may be sterile and/or substantially isotonic and/or in full compliance with all Good Manufacturing Practice regulations of the U.S. Food and Drug Administration.

VII. Routes of Administration of Compounds and Compositions of the Invention The compounds may be administered by any route, including but not limited to oral, rectal, sublingual, buccal, ocular, pulmonary, and parenteral administration, or as an oral or nasal spray (e.g. inhalation of nebulized vapors, droplets, or solid particles). Parenteral administration includes, for example, intravenous, intramuscular, intraarterial, intraperitoneal, intranasal, intravaginal, intravesical (e.g., to the bladder), intradermal, transdermal, topical or subcutaneous administration. Also contemplated within the scope of the invention is the instillation of a drug in the body of the patient in a controlled formulation, with systemic or local release of the drug to occur at a later time. For example, the drug may be localized in a depot for controlled release to the circulation, or for release to a local site of tumor growth.

One or more compounds useful in the practice of the present inventions may be administered simultaneously, by the same or different routes, or at different times during treatment. The compounds may be administered before, along with, or after other medications, including other antiproliferative compounds.

The treatment may be carried out for as long a period as necessary, either in a single, uninterrupted session, or in discrete sessions. The treating physician will know how to increase, decrease, or interrupt treatment based on patient response. According to one embodiment, treatment is carried out for from about four to about sixteen weeks. The treatment schedule may be repeated as required.

VIII. Examples

The following non-limiting examples are provided to illustrate the invention. The illustrated synthetic pathways are applicable to other embodiments of the invention. The synthetic procedures described as "general methods" describe what it is believed will be typically effective to perform the synthesis indicated. However, the person skilled in the art will appreciate that it may be necessary to vary the procedures for any given embodiment of the invention. For example, reaction monitoring, such as by using thin layer chromatography (TLC), or HPLC may be used to determine the optimum reaction time. Products may be purified by conventional techniques that will vary, for example, according to the amount of side products produced and the physical properties of the compounds. On a laboratory scale, recrystallisation from a suitable solvent, column chromatography, normal or reverse phase HPLC, or distillation are all techniques which may be useful. The person skilled in the art will appreciate how to vary the reaction conditions to synthesize any given compound within the scope of the invention without undue experimentation. See, e.g., *Vogel's Textbook of Practical Organic Chemistry*, by A. I. Vogel, et al, *Experimental Organic Chemistry: Standard and Microscale*, by L. M. Harwood et al. ($2^{nd}$ Ed., Blackwell Scientific Publications, 1998), and *Advanced Practical Organic Chemistry*, by J. Leonard, et al. (2" Edition, CRC Press 1994).

Example 1

Synthesis of 8-cyclopentyl-2-((4-(4-methylpiperazin-1-yl)phenyl)amino)-7-oxo-7,8-dihydropyrido[2,3-d]pyrimidine-6-carbonitrile 8-cyclopentyl-2-((4-(4-methylpiperazin-1-yl)phenyl)amino)-7-oxo-7,8-dihydropyrido[2,3-d]pyrimidine-6-carbonitrile was prepared according to following procedure.

A. 4-Cyclopentylamino-2-methylsulfanyl-pyrimidine-5-carboxylic acid ethyl ester (7)

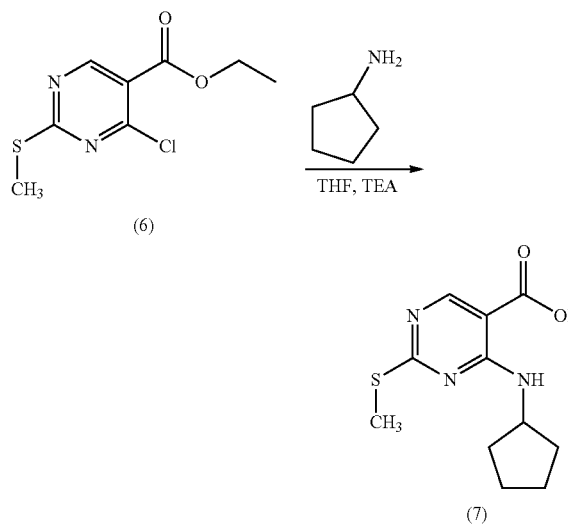

Commercially available 4-chloro-2-methylsulfanyl-pyrimidine-5-carboxylic acid ethyl ester (6) (25 g, 107 mmol) was dissolved in THF. Subsequently, triethylamine (32.6 g, 322 mmol) and cyclopentylamine (10 g, 117 mmol) were added to the reaction mixture. The combination was stirred over night at room temperature. Precipitated salts were filtered away from solvent and discarded. The collected solvent was then evaporated in vacuo to give an oil. The resultant oil was dissolved in ethyl acetate, washed with sodium bicarbonate, and then dried over Na$_2$SO$_4$. The drying aid was filtered away and the resultant solvent was evaporated under vacuum to give 23.3 g of product (7). $^1$H NMR (300 MHz, CDCl$_3$), δ 8.60 (s, 1H), 8.25 (br s, 1H), 4.49-4.54 (m, 1H), 4.30 (q, 2H), 2.52 (s, 3H), 2.00-2.10 (m, 2H), 1.50-1.79 (m, 6H), 1.35 (t, 3H).

B. (4-Cyclopentylamino-2-methylsulfanyl-pyridine-5-yl)-methanol (8)

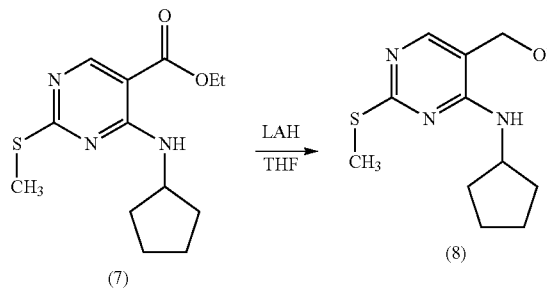

Lithium aluminum hydride (10 g, 35.5 mmol) was suspended in THF under a nitrogen atmosphere and cooled with dry ice. 4-Cyclopentylamino-2-methylsulfanyl-pyrimidine-5-carboxylic acid ethyl ester (7), (2.02 g, 53.3 mmol) was dissolved in THF and added dropwise to the cooled LAH solution, keeping the reaction temperature below −20° C. for the duration of the addition. The reaction was subsequently brought to room temperature and stirred for 5 h. After stirring, the reaction was quenched by the addition of water (5 ml), 15% NaOH (10 ml) and then water (15 ml) again. A white solid that precipitated was filtered away and the filtrate evaporated in vacuo to provide product (8) as a yellow solid (7.2 g). Product (8) was used without further purification or characterization.

C. 4-Cyclopentylamino-2-methylsulfanyl-pyrimidine-5-carbaldehyde (9)

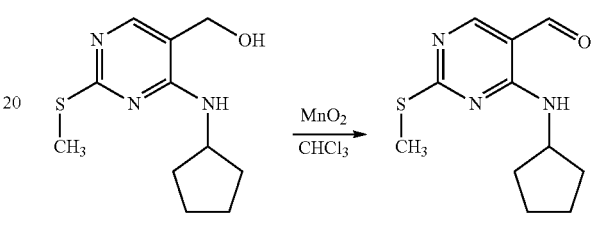

(4-Cyclopentylamino-2-methylsulfanyl-pyridine-5-yl)-methanol (8), (5 g 20.8 mmol) was dissolved in chloroform to which MnO$_2$ (10.39 g 119 mmol) was added. The reaction was then stirred over night. An additional portion of MnO$_2$ (2.7 g, 31.3 mmol) was added and the reaction was stirred for an additional 12 h. MnO$_2$ was removed by filtration through a Celite pad that was washed well with chloroform. The chloroform was evaporated under vacuum to give the desired product (9) as a thick liquid (4.7 g) which became solid upon standing for some time. $^1$H NMR (300 MHz, CDCl$_3$), δ 9.65 (s, 1H), 8.60 (br s, 1H), 8.25 (s, 1H), 4.49-4.54 (m, 1H), 2.52 (s, 3H), 2.01-2.12 (m, 2H), 1.50-1.82 (m, 6H).

D. 8-cyclopentyl-2-(methylthio)-7-oxo-7,8-dihydropyrido[2,3-d]pyrimidine (10)

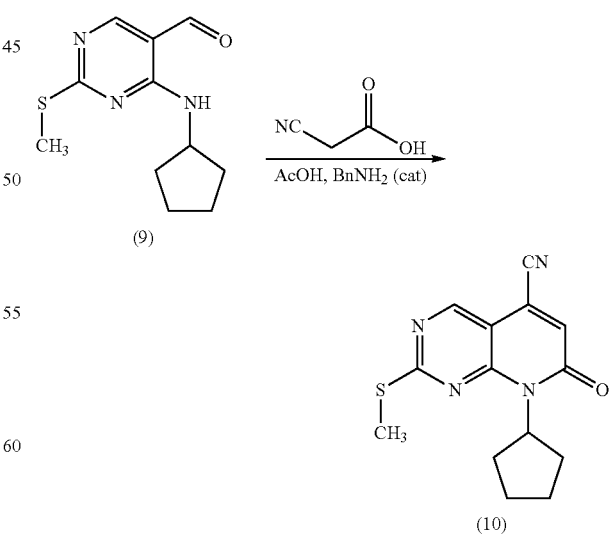

A mixture of 4-cyclopentylamino-2-methylsulfanyl-pyrimidine-5-carbaldehyde (9), (1 g, 4.2 mmol), 1.2 equivalent of cyanoacetic acid, and a catalytic amount of benzylamine was taken into acetic acid and refluxed for about 6 h. After completion of the reaction by TLC, the reaction mixture was cooled to room temperature and product precipitated from the reaction mixture. Additional product was precipitated from the reaction mixture via the addition of hexane. The resultant solid was collected, washed with saturated NaHCO$_3$, water, and subsequently dried under vacuum. The resultant crude product (10) was recrystallized in 2-propanol.

E. 8-cyclopentyl-2-(methylsulfinyl)-7-oxo-7,8-dihydropyrido[2,3-d]pyrimidine (11)

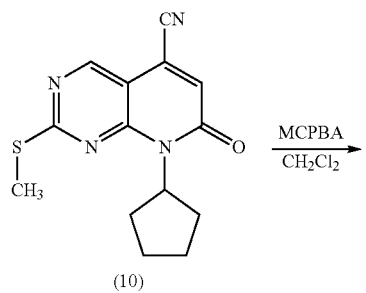

(10)

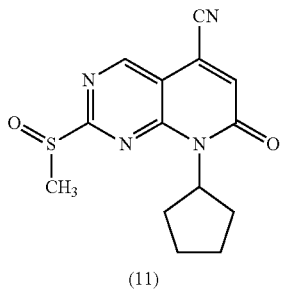

(11)

A solution of 8-cyclopentyl-2-(methylthio)-7-oxo-7,8-dihydropyrido[2,3-d]pyrimidine (10), (3.5 mmol) and MCPBA (5.25 mmol) in CH$_2$Cl$_2$ was stirred at room temperature for about 12 h. After completion of the reaction, the reaction mixture was washed with saturated NaHCO$_3$. The organic layer was dried over Na$_2$SO$_4$, filtered away from the drying agent, and concentrated to give the desired product (11) which was used without further purification.

F. 8-cyclopentyl-2-((4-(4-methylpiperazin-1-yl)phenyl)amino)-7-oxo-7,8-dihydropyrido[2,3-d]pyrimidine-6-carbonitrile (12)

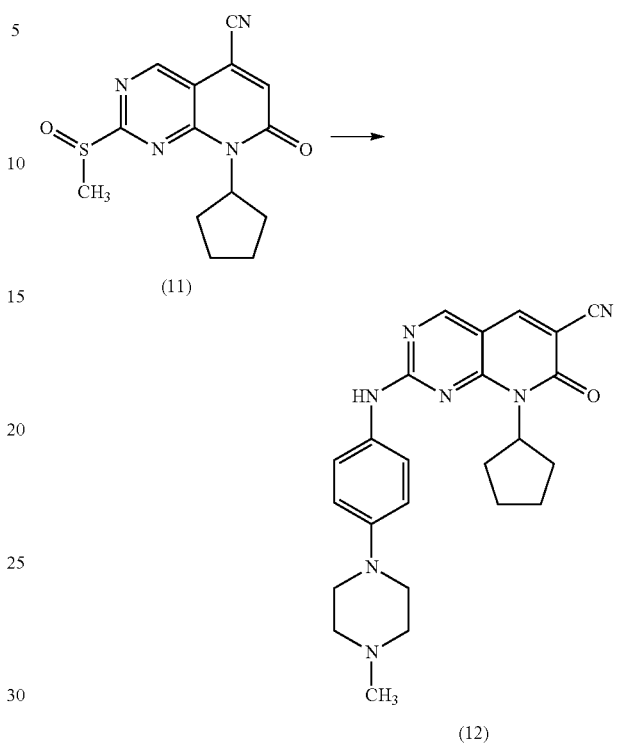

A mixture of 8-cyclopentyl-2-(methylsulfinyl)-7-oxo-7,8-dihydropyrido[2,3-d]pyrimidine (11), (1.65 mmol) and 4-(4-methylpiperazin-1-yl)aniline (2 mmol) in toluene was stirred at 100° C. over night. The reaction mixture was cooled and a solid that had formed was collected by filtration. The solids were then washed with toluene and dried to give the desired product (12). $^1$H NMR (300 MHz, CDCl$_3$), 8.55 (s, 1H), 7.79 (s, 1H), 7.40-7.45 (m, 2H), 6.91-6.99 (m, 2H), 3.23-3.27 (m, 4H), 2.63-2.66 (m, 4H), 2.43 (s, 3H), 2.21-2.30 (m, 2H), 1.85 (br s, 4H), 1.62 (br s, 2H). m.p: 290-292° C.

Examples 2 to 6

Compounds 13-16, show in Table 1, below, were prepared by following the general procedures of Schemes 1-5, as exemplified by the preparation of compound (12). Table 1 further includes $^1$H NMR spectral data and melting point data for compounds 13-16.

TABLE 1

| Cpd. # | Compound | Compound Name | $^1$H NMR and MP Data |
|---|---|---|---|
| 13 | | 8-cyclopentyl-2-((4-morpholinophenyl)amino)-7-oxo-7,8-dihydropyrido[2,3-d]pyrimidine-6-carbonitrile | 8.55 (s, 1H), 7.98 (s, 1H), 7.43-7.48 (m, 2H), 6.93-6.99 (m, 2H), 5.82-5.89 (m, 1H), 3.87-3.92 (m, 4H), 3.15-3.22 ((m, 4H), 2.22-2.31 (m, 2H), 1.80-1.91 (m, 4H), 1.59-1.68 (m, 2H). MP: 294-296° C. |

TABLE 1-continued

| Cpd. # | Compound | Compound Name | ¹H NMR and MP Data |
|---|---|---|---|
| 14 | (structure) | 8-cyclopentyl-2-((3,5-dimethoxyphenyl)amino)-7-oxo-7,8-dihydropyrido[2,3-d]pyrimidine-6-carbonitrile | 8.60 (s, 1H), 7.99 (s, 1H), 6.83-6.84 (m, 2H), 6.30-6.31 (m, 2H), 5.88-5.94 (m, 1H), 3.82 (s, 6H), 2.23-2.36 (m, 2H), 2.05-2.18 (m, 2H), 1.83-1.93 (m, 2H), 1.62-1.64 (m, 2H). MP: 150-151° C. |
| 15 | (structure) | 8-cyclopentyl-7-oxo-2-((3,4,5-trimethoxyphenyl)amino)-7,8-dihydropyrido[2,3-d]pyrimidine-6-carbonitrile | 8.59 (s, 1H), 8.01 (s, 1H), 6.91 (s, 2H), 5.93-5.99 (m, 1H), 3.90 (s, 3H), 3.87 (s, 3H), 2.23-2.32 (m, 2H), 2.03-2.14 (m, 2H), 1.85-1.92 (m, 2H), 1.52-1.58 (m, 2H). MP: 169-170° C. |
| 16 | (structure) | 8-cyclohexyl-2-((4-(4-methylpiperazin-1-yl)phenyl)amino)-7-oxo-7,8-dihydropyrido[2,3-d]pyrimidine-6-carbonitrile | 8.53 (s, 1H), 7.94 (s, 1H), 7.45-7.66 (m, 2H), 6.95-6.98 (m, 2H), 5.43-5.47 (m, 1H), 3.22-3.26 (m, 4H), 2.62-2.65 (m, 4H), 2.39 (s, 3H), 1.88 (br s, 2H), 1.64 (br s, 4H), 1.33 (br s, 4H). MP: 279-280° C. |

Example 7

Cytotoxicity Assay For 8-cyclopentyl-2-((4-(4-methylpiperazin-1-yl)phenyl)amino)-7-oxo-7,8-dihydropyrido[2,3-d]pyrimidine-6-carbonitrile Cells ($1 \times 10^5$) were plated into 6-well dishes and 24 h later 8-cyclopentyl-2-((4-(4-methylpiperazin-1-yl)phenyl)amino)-7-oxo-7,8-dihydropyrido[2,3-d]pyrimidine-6-carbonitrile (12) was added at five different concentrations over a 2 log dilution (1-100 μM). The total number of viable cells was determined after 96 h of continuous treatment by staining with trypan blue and counting the number of non-staining cells (viable) remaining in each well using a hemacytometer. The percentage of viable cells remaining was calculated as follows: # viable cells (compound treated)/# viable cells (DMSO treated)*100. The $GI_{50}$ (the concentration of drug resulting in 50% net loss of growth inhibition) was determined. The results are shown in Table 2.

TABLE 2

| CELL LINE | Tumor Type | GI 50 (μM) |
|---|---|---|
| K562 | CML | 0.5 |
| DU145 | PROSTATE | 0.75 |
| BT474 | ErbB2 + Breast | 0.25 |
| SK-BR-3 | ErbB2 + Breast | 0.6 |
| MCF-7 | ER + Breast | 0.15 |
| BT20 | Breast | 0.1 |
| MDA-MB-468 | BREAST (triple neg; RB neg) | 1.5 |
| Z138C | MCL | 0.025 |
| GRANTA-519 | MCL | 0.075 |
| SK-OV-3 | Ovarian | 0.75 |
| U87 | Glioblastoma | 0.1 |
| MIA-PaCa-2 | Pancreatic | 0.25 |
| HCT-15 | Colon (MDR elevated) | 0.4 |
| COLO-205 | Colon | 0.2 |
| HELA | Cervical | 0.75 |
| A549 | NSCLC | 0.2 |
| N417 | SCLC | 0.25 |
| N87 | Gastric(ErbB2+) | 0.9 |
| SNU-5 | Gastric | 0.2 |
| SNU-398 | Gastric | 0.5 |

TABLE 2-continued

| CELL LINE | Tumor Type | GI 50 (µM) |
|---|---|---|
| SNU-449 | Gastric | 0.75 |
| SNU-475 | Gastric | 0.3 |
| U266 | Multiple Myeloma | 0.2 |
| RAJI | B-Cell Lymphoma | 0.25 |
| JURKAT | T-Cell Lymphoma | 0.15 |
| DLD-1 | COLO-RECTAL | 0.1 |
| SW480 | COLO-RECTAL | 0.1 |

Example 8

ARK5 Kinase Assay 20 ng His-tagged full length ARK5 (Invitrogen PV4127), a protein kinase, was diluted into kinase buffer (25 mM HEPES pH 7.5, 10 mM $MgCl_2$, 0.5 mM EGTA, 0.5 mM $Na_3VO_4$, 5 mM β Glycerophosphate, 2.5 mM DTT, 0.01% Triton X-100) and incubated with the indicated concentration of a compound of Table 3 at room temperature for 30 minutes. The kinase reactions were then initiated by the addition of 1 µg (3.28 µM) CHKtide substrate peptide (Upstate 12-414), 1 µM ATP and 10 µCi $γ^{32}$ P-ATP. The reactions were incubated at 30° C. for 10 minutes.

Subsequently, the reactions were stopped by adding 3% phosphoric acid. A 10 µl aliquot was then transferred to an appropriate area of a p30 filtermat. The filtermat was allowed to dry for 20 minutes at room temperature and then washed three times with 75 mM phosphoric acid and twice with methanol. The filtermat was then dried for 20 minutes at room temperature. The filtermat was then exposed to X ray film or read in a scintillation counter. The scintillation counting values were plotted as function of log drug concentration using Prism 4 Graph pad software and $IC_{50}$ values determined by plotting sigmoidal non-linear regression curves with variable slope.

As shown in Table 3, the compounds of Examples 1-6 substantially inhibited the kinase activity of ARK5. Comparative examples that lacked the nitrile functionality of compounds of the invention, showed little to no ability to inhibit ARK5.

TABLE 3

ARK5 Inhibition Assay

| Cpd. # | Compound | $IC_{50}$ (nM) |
|---|---|---|
| 12 | 8-cyclopentyl-2-((4-(4-methylpiperazin-1-yl)phenyl)amino)-7-oxo-7,8-dihydropyrido[2,3-d]pyrimidine-6-carbonitrile | 27.3 |
| 15 | 8-cyclopentyl-7-oxo-2-((3,4,5-trimethoxyphenyl)amino)-7,8-dihydropyrido[2,3-d]pyrimidine-6-carbonitrile | 49.8 |
| 16 | 8-cyclohexyl-2-((4-(4-methylpiperazin-1-yl)phenyl)amino)-7-oxo-7,8-dihydropyrido[2,3-d]pyrimidine-6-carbonitrile | 43.41 |
| 13 | 8-cyclopentyl-2-((4-morpholinophenyl)amino)-7-oxo-7,8-dihydropyrido[2,3-d]pyrimidine-6-carbonitrile | 75 |
| 14 | 8-cyclopentyl-2-((3,5-dimethoxyphenyl)amino)-7-oxo-7,8-dihydropyrido[2,3-d]pyrimidine-6-carbonitrile | 75 |
| Comp. Ex. 1 | 8-cyclopentyl-2-((4-(4-methylpiperazin-1-yl)phenyl)amino)-6-(methylsulfonyl)pyrido[2,3-d]pyrimidin-7(8H)-one | >10,000 |
| Comp. Ex. 2 | 6-((4-chlorophenyl)sulfonyl)-8-cyclopentyl-2-((4-(4-methylpiperazin-1-yl)phenyl)amino)pyrido[2,3-d]pyrimidin-7(8H)-one | >10,000 |

TABLE 3-continued

ARK5 Inhibition Assay

| Cpd. # | Compound | $IC_{50}$ (nM) |
|---|---|---|
| Comp. Ex. 3 | 6-((4-chlorophenyl)sulfonyl)-8-cyclohexyl-2-((4-(4-methylpiperazin-1-yl)phenyl)amino)pyrido[2,3-d]pyrimidin-7(8H)-one | 1000 |
| Comp. Ex. 4 | 8-cyclopentyl-2-((3,4-dimethoxyphenyl)amino)pyrido[2,3-d]pyrimidin-7(8H)-one | >1000 |
| Comp. Ex. 5 | 8-cyclopentyl-2-((2,4-dimethoxyphenyl)amino)pyrido[2,3-d]pyrimidin-7(8H)-one | >5000 |

Example 9

In Vivo Efficacy of 8-cyclopentyl-2-((4-(4-methylpiperazin-1-yl)phenyl)amino)-7-oxo-7,8-dihydropyrido[2,3-d]pyrimidine-6-carbonitrile Against Human Colon Cancer Colo-205 fragments were implanted into female athymic nude mice and were grown to an average size of 150 $mm^3$. Subsequently, the mice were treated with Placebo (n=10) or 100 mg/kg of 8-cyclopentyl-2-((4-(4-methylpiperazin-1-yl)phenyl)amino)-7-oxo-7,8-dihydropyrido[2,3-d]pyrimidine-6-carbonitrile hydrochloride formulated in sterile water (N=10) by IP injection according to the following schedule: QD days 1-21; off days 22 and 23; dosage resumed days 24-28. One mouse was euthanized on day 25 due to non-drug related peritonitis. Tumor volumes were determined and the median (+/−SEM) were plotted against day of treatment. See FIG. 1.

Example 10

Comparison of Kinase Inhibition of 8-cyclopentyl-2-((4-(4-methylpiperazin-1-yl)phenyl)amino)-7-oxo-7,8-dihydropyrido[2,3-d]pyrimidine-6-carbonitrile to Kinase Inhibition of PD0332991

PD0332991 has the structure:

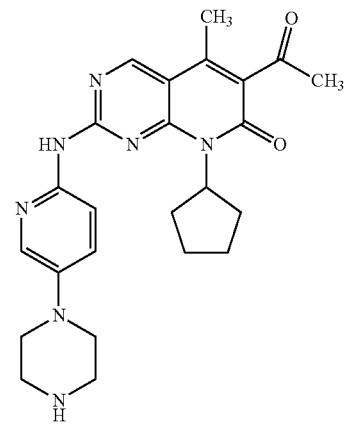 [SMILES: CC(=O)c1c(C)c2cnc(Nc3ccc(N4CCNCC4)cn3)nc2n(C2CCCC2)c1=O]

According to the National Cancer Institute, PD0332991 is an orally available pyridopyrimidine-derived cyclin-dependent kinase (CDK) inhibitor with potential antineoplastic activity. In particular, PD-0332991 selectively inhibits cyclin-dependent kinases (particularly Cdk4/cyclin D1 kinase), which may inhibit retinoblastoma (Rb) protein phosphorylation, which prevents Rb-positive tumor cells from entering the S phase of the cell cycle (arrest in the G1 phase). This results in suppression of DNA replication and decreased tumor cell proliferation.

The compounds in Table 4 were tested for the ability to inhibit the kinase activity of the listed protein kinases. Compounds were tested in 5 dose $IC_{50}$ mode with 10-fold serial dilution starting at 10 µM. Staurosporine, a known protein kinase inhibitor, was tested in 5 dose $IC_{50}$ mode with 3-fold serial dilution starting at 20 µM. Reactions were carried out in 10 µM ATP.

As observed from Table 4,8-cyclopentyl-2-((4-(4-methylpiperazin-1-yl)phenyl)amino)-7-oxo-7,8-dihydropyrido[2,3-d]pyrimidine-6-carbonitrile, has a significantly different protein kinase inhibition profile as compared to PD0332991. The compound of the invention is a multi-specific protein kinase inhibitor, being inhibitory against a broader range of protein kinases than PD0332991.

All references cited herein are incorporated by reference in their entirety. The present invention may be embodied in other specific forms without departing from the spirit or essential attributes thereof and, accordingly, reference should

TABLE 4

| | $IC_{50}$ (nM) | | |
|---|---|---|---|
| Kinase | PD0332991 | 8-cyclopentyl-2-((4-(4-methylpiperazin-1-yl)phenyl)amino)-7-oxo-7,8-dihydropyrido[2,3-d]pyrimidine-6-carbonitrile | Staurosporine |
| ABL1 | ND | 75.64 | 66.37 |
| ABL2/ARG | ND | 91.57 | 21.58 |
| ARK5 | 3388.00 | 7.85 | <1.0 |
| c-Kit | >10000 | 407.50 | 28.47 |
| c-MET | ND | ND | 378.10 |
| c-Src | ND | 93.01 | 1.49 |
| CDK2/cyclinA | 5986.00 | 97.32 | <1.0 |
| CDK2/cyclinE | >10000 | 769.50 | 2.13 |
| CDK3/cyclinE | ND | 3219.00 | 10.13 |
| CDK4/Cyclin D1 | 7.41 | 4.00 | 22.14 |
| CDK4/Cyclin D3 | 25.81 | 21.23 | 47.22 |
| CDK5/p25 | 5987.00 | 263.70 | 1.91 |
| CDK5/p35 | 5928.00 | 181.50 | 1.89 |
| CDK6/cyclinD1 | 12.75 | 18.39 | 14.19 |
| CDK6/cyclinD3 | 36.48 | 38.67 | 128.00 |
| CDK7/cyclinH/MNAT1 | ND | >10000 | 195.80 |
| CDK9/cyclin K | 351.60 | 27.10 | 7.52 |
| CDK9/cyclinT1 | 2245.00 | 85.36 | 12.55 |
| EPHA1 | ND | 37.13 | 55.56 |
| EPHA2 | ND | 113.70 | 108.20 |
| EphB1 | ND | 26.74 | 49.32 |
| EphB2/HEK5 | ND | 130.30 | 50.48 |
| EphB4 | ND | 120.40 | 165.30 |
| FGFR1 | ND | 68.15 | 3.44 |
| FGFR2 | ND | 54.79 | 1.70 |
| FGFR3 | ND | 123.60 | 6.45 |
| FGFR4 | ND | 3548.00 | 104.60 |
| FGR | >10000 | 112.20 | <1.0 |
| FLTINEGFRI | >10000 | 94.14 | 4.32 |
| FLT3 | 324.20 | 13.57 | <1.0 |
| FLT4NEGFR3 | >10000 | 63.51 | 4.99 |
| FMS | 1990.00 | 1.46 | 1.14 |
| FRK/PTK5 | ND | 574.70 | 51.44 |
| FYN | >10000 | 26.59 | 2.26 |
| LCK | >10000 | 50.41 | 2.07 |
| LIMK1 | ND | 70.84 | 3.26 |
| LOK/STK10 | 2443.00 | 180.90 | 4.68 |
| LYN | >10000 | 68.53 | <1.0 |
| LYNB | ND | 6645.00 | 27.33 |
| NLK | ND | 45.27 | 51.44 |
| PAK3 | ND | 1929.00 | <1.0 |
| PDGFRb | 980.30 | 2.64 | <1.0 |
| PKCmu | 126.50 | 142.10 | 1.63 |
| PKCnu/PRK D3 | 60.87 | 55.76 | <1.0 |
| PKG2/PRKG2 | ND | ND | 1.46 |
| RIPK2 | ND | 40.75 | 138.50 |
| SIK2/SNF1LK2 | ND | 96.79 | 33.78 |
| SNARK/NUAK2 | 8667.00 | 20.71 | 3.08 |
| TAOK1 | 2844.00 | 78.68 | <1.0 |
| TAOK2ITA01 | 1781.00 | 69.64 | 4.41 |
| TBK1 | ND | 71.78 | <1.0 |
| TGFbR2 | ND | 62.28 | 17780.00 |
| TTK | 696.60 | 155.80 | 71.49 |
| YES/YES1 | 3675.00 | 38.08 | <1.0 |
| ZAK/MLTK | ND | 29.49 | 19480.00 |

ND = Not Done

What is claimed is:

1. A compound according to Formula I, or a pharmaceutically acceptable salt thereof,

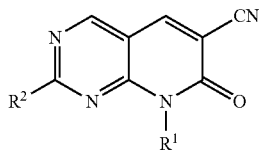

Formula I wherein
R$^1$ is (C$_1$-C$_6$)alkyl or (C$_3$-C$_8$)cycloalkyl;
R$^2$ is 4-(4-methylpiperazin-1-yl)anilinyl, 4-morpholinoanilinyl, or

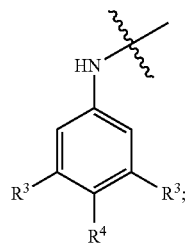

R$^3$ is independently at each occurrence (C$_1$-C$_6$)alkoxy; and
R$^4$ is H or (C$_1$-C$_6$)alkoxy.

2. The compound of claim 1, wherein R$^2$ is

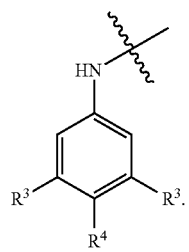

3. The compound of claim 2, wherein R$^1$ is cyclopentyl.
4. The compound of claim 3, wherein each occurrence of R$^3$ is methoxy.
5. The compound of claim 4, wherein R$^4$ is hydrogen.
6. The compound of claim 4, wherein R$^4$ is methoxy.
7. The compound of claim 1, wherein R$^2$ is 4-(4-methylpiperazin-1-yl)anilinyl.
8. The compound of claim 7, wherein R$^1$ is (C$_3$-C$_8$)cycloalkyl.
9. The compound of claim 8, wherein R$^1$ is cyclopentyl or cyclohexyl.
10. The compound of claim 1, wherein R$^2$ is 4-morpholinoanilinyl.
11. The compound of claim 10, wherein R$^1$ is cyclopentyl.
12. The compound of claim 1, wherein the compound is selected from the group consisting of
8-cyclopentyl-2-((4-(4-methylpiperazin-1-yl)phenyl)amino)-7-oxo-7,8-dihydropyrido[2,3-d]pyrimidine-6-carbonitrile;
8-cyclohexyl-2-((4-(4-methylpiperazin-1-yl)phenyl)amino)-7-oxo-7,8-dihydropyrido[2,3-d]pyrimidine-6-carbonitrile;
8-cyclopentyl-2-((3,5-dimethoxyphenyl)amino)-7-oxo-7,8-dihydropyrido[2,3-d]pyrimidine-6-carbonitrile;
8-cyclopentyl-7-oxo-2-((3,4,5-trimethoxyphenyl)amino)-7,8-dihydropyrido[2,3-d]pyrimidine-6-carbonitrile;
8-cyclopentyl-2-((4-morpholinopheny)amino)-7-oxo-7,8-dihydropyrido[2,3-d]pyrimidine-6-carbonitrile; and
pharmaceutically acceptable salts thereof.

13. The compound of according to claim 12, wherein the compound is 8-cyclopentyl-2-((4-(4-methylpiperazin-1-yl)phenyl)amino)-7-oxo-7,8-dihydropyrido[2,3-d]pyrimidine-6-carbonitrile or a pharmaceutically acceptable salt thereof.

14. A pharmaceutical composition comprising a pharmaceutically acceptable carrier and a compound according to claim 1, or a pharmaceutically acceptable salt thereof.

15. A pharmaceutical composition according to claim 14, wherein the compound according to claim 1 is selected from the group consisting of
8-cyclopentyl-2-((4-(4-methylpiperazin-1-yl)phenyl)amino)-7-oxo-7,8-dihydropyrido[2,3-d]pyrimidine-6-carbonitrile;
8-cyclohexyl-2-((4-(4-methylpiperazin-1-yl)phenyl)amino)-7-oxo-7,8-dihydropyrido[2,3-d]pyrimidine-6-carbonitrile;
8-cyclopentyl-2-((3,5-dimethoxyphenyl)amino)-7-oxo-7,8-dihydropyrido[2,3-d]pyrimidine-6-carbonitrile;
8-cyclopentyl-7-oxo-2-(3,4,5-trimethoxypheny)amino)-7,8-dihydropyrido[2,3-d]pyrimidine-6-carbonitrile;
8-cyclopentyl-2-((4-morpholinopheny)amino)-7-oxo-7,8-dihydropyrido[2,3-d]pyrimidine-6carbonitrile; and
pharmaceutically acceptable salts thereof.

16. A method of inducing apoptosis of cancer cells in an individual afflicted with cancer, comprising administering to the individual an effective amount of at least one compound according to claim 1, or a pharmaceutically acceptable salt thereof.

17. The method of claim 16, wherein the cancer cells are tumor cells.

18. A method according to claim 17, wherein the tumor cells are selected from the group consisting of ovarian, cervical, uterine, vaginal, breast, prostate, testicular, lung, renal, colorectal, stomach, adrenal, mouth, esophageal, hepatic, gall bladder, bone, lymphatic, eye, skin and brain tumor cells.

19. A method of inhibiting kinase activity in a mammal in need of such treatment, said method comprising administering a therapeutically effective amount of a compound of claim 1, or a pharmaceutically acceptable salt thereof.

20. The method according to claim 19, wherein the compound is 8-cyclopentyl-2-((4-(4-methylpiperazin-1-yl)phenyl)amino)-7-oxo-7,8-dihydropyrido[2,3-d]pyrimidine-6-carbonitrile, or a pharmaceutically acceptable salt thereof.

21. A process for preparing a compound according to claim 1, said process comprising treating a compound of Formula II

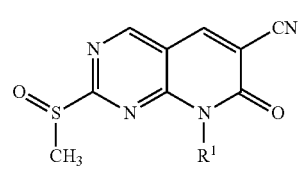

Formula II with an amine selected from the group consisting of 4-(4-methylpiperazin-1-yl)aniline, 4-morpholinoaniline, and

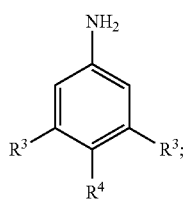

wherein
$R^1$ is $(C_1\text{-}C_6)$alkyl or $(C_3\text{-}C_8)$cycloalkyl;
$R^3$ is independently at each occurrence $(C_1\text{-}C_6)$alkoxy; and
$R^4$ is H or $(C_1\text{-}C_6)$alkoxy,
obtaining a compound according to claim 1, and optionally converting said compound to a pharmaceutically acceptable salt thereof.

22. The process of claim 21, wherein the amine is 4-(4-methylpiperazin-1-yl)aniline.

23. The process of claim 22, wherein $R^1$ is $(C_1\text{-}C_6)$alkyl.

24. The process of claim 22, wherein $R^1$ is $(C_3\text{-}C_8)$cycloalkyl.

25. The process of claim 24, wherein $R^1$ is cyclopentyl.

26. A method for treating an individual for cancer comprising administering to the individual an effective amount of 8-cyclopentyl-2-((4-(4-methylpiperazin-1-yl)phenyl) amino)-7-oxo-7,8-dihydropyrido [2,3-d]pyrimidine-6-carbonitrile, or a pharmaceutically acceptable salt thereof, wherein the cancer is ovarian cancer; cervical cancer; breast cancer; prostate cancer; lung cancer; colorectal cancer; brain cancer; pancreatic cancer; gastric cancer; multiple myeloma; lymphoma; or leukemia.

27. The method according to claim 26, wherein the leukemia is selected from the group consisting of acute myeloid leukemia, chronic myeloid leukemia, acute lymphoid leukemia, and chronic lymphoid leukemia.

* * * * *